(12) United States Patent
Pulley

(10) Patent No.: US 6,182,294 B1
(45) Date of Patent: Feb. 6, 2001

(54) HEAD COVERING WITH HEAT GENERATING MEANS

(76) Inventor: Debra Pulley, 440 NE. 5th Ave., Camas, WA (US) 98607

(*) Notice: Under 35 U.S.C. 154(b), the term of this patent shall be extended for 0 days.

(21) Appl. No.: 09/597,212

(22) Filed: Jun. 20, 2000

(51) Int. Cl.$^7$ .............................. A42B 1/18; A42B 19/02
(52) U.S. Cl. ...................................... 2/171; 2/174
(58) Field of Search ............................ 2/171, 171.2, 172, 2/174, 204, 209.13, 209.14, 175.4

(56) References Cited

U.S. PATENT DOCUMENTS

| | | | | |
|---|---|---|---|---|
| 2,783,806 | * | 3/1957 | Andreadis | 2/174 |
| 2,804,695 | * | 9/1957 | Scott | 2/174 |
| 4,382,446 | * | 5/1983 | Truelock et al. | 607/110 |
| 5,327,585 | * | 7/1994 | Karlan | 2/174 |
| 5,557,807 | * | 9/1996 | Hujar et al. | 2/171.2 |
| 5,850,636 | * | 12/1998 | Reuven | 2/174 |

* cited by examiner

Primary Examiner—Gloria M. Hale
(74) Attorney, Agent, or Firm—Risto A. Rinne, Jr.

(57) ABSTRACT

Head covering with heat generating means comprised of an insulated adjustable head covering, a rigid cross brace attached to the upper inside surface of the head covering, a plurality of heat generating packets removably attached to the cross brace, the heat generating packets comprised of a combination of iron powder, water, salt, activated charcoal and vermiculite, and the heat generating packets packed in an air tight package and which activate when removed from the air tight package. A preferred embodiment includes wherein the heat generating packets produce heat of approximately 126 degrees farenheight lasting for up to three hours.

3 Claims, 2 Drawing Sheets

US 6,182,294 B1

HEAD COVERING WITH HEAT GENERATING MEANS

BACKGROUND OF THE INVENTION

This invention relates generally to the field of head coverings, and more particularly to a head covering with heat generating means.

Hair conditioning products are known. Recently a category of hair conditioning product has been introduced into the market place that requires the user to introduce heat to properly activate the conditioning qualities of the hair conditioning product. One manufacturer of such a product is Helene Curtis who makes a heat activated conditioner named Thermasilk. To help with the activation of the product, the manufacturer suggests that the user either use a hair dryer to heat the hair or to wrap the head with a plastic material to help retain the heat generated from the scalp area. Both these suggestions have their limitations. The hair dryer solution requires the user to hold his or her arm up in the air for extended periods and precludes the user from doing any other activity at the time of hair heating. The plastic head wrap solution works with the heat generated from the users head. Since body temperature is nintey eight degrees, the heat within the wrap can not exceed that temperature. Most of the heat activated conditioners work best at temperatures higher than body temperature.

SUMMARY OF THE INVENTION

The primary object of the invention is to provide a head covering means that has a heat generating compound built in, that when activated, provides a warm environment to facilitate the use of heat activated hair conditioners.

Other objects and advantages of the present invention will become apparent from the following descriptions, taken in connection with the accompanying drawings, wherein, by way of illustration and example, an embodiment of the present invention is disclosed.

Head Covering with Heat Generating Means comprising: an insulated adjustable head covering, a rigid cross brace, a plurality of heat generating packets removably attached to said cross brace, said heat generating packets comprised of a combination of iron powder, water, salt, activated charcoal and vermiculite, and said heat generating packets packed in an air tight package and which activate when removed from said air tight package.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
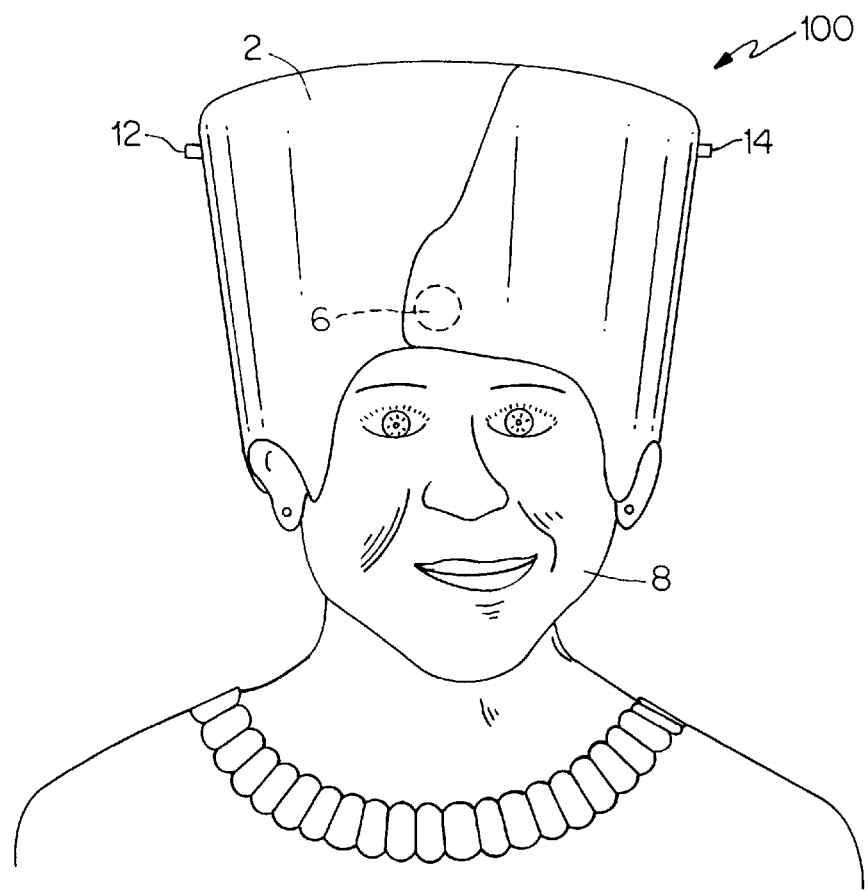
FIG. 1 is a front view of a person wearing the head covering of the present invention
Figure 2:
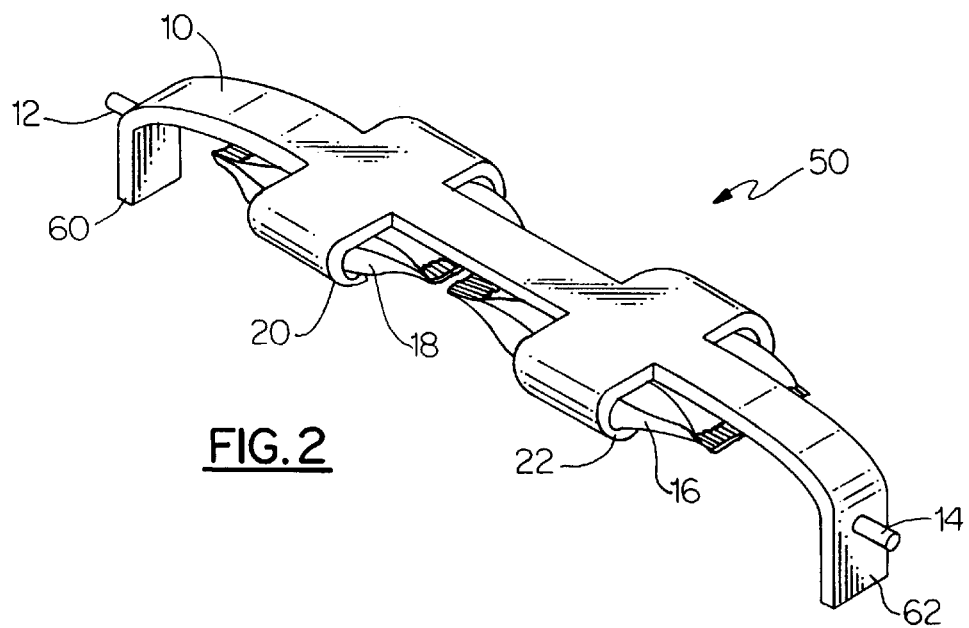
FIG. 2 is a perspective view of the cross brace of the present invention
Figure 3:
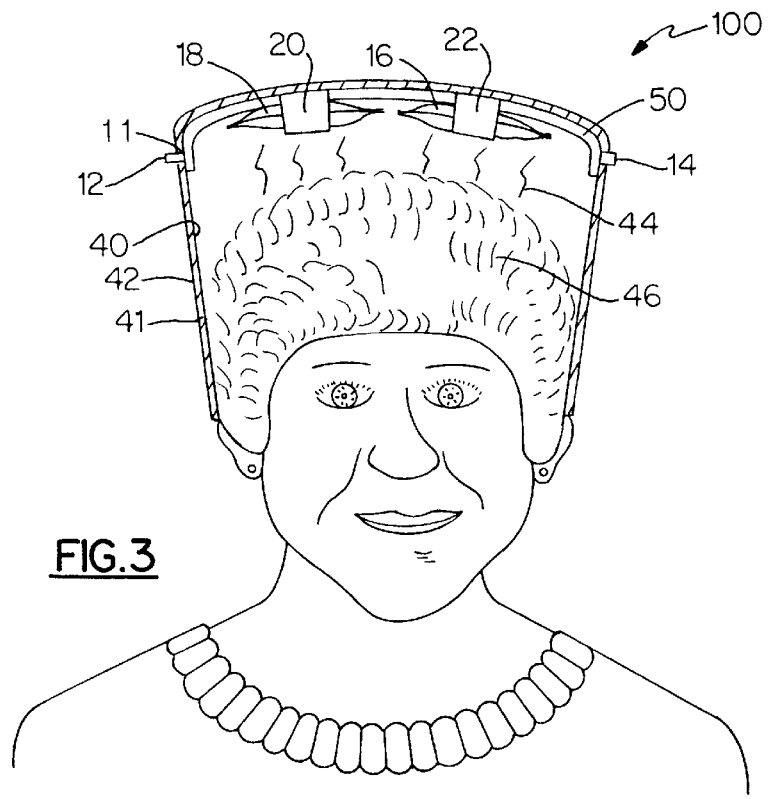
FIG. 3 is a front section view of a person wearing the present invention
Figure 4:
FIG. 4 is a side view of a person wearing the head covering of the present invention.

Referring now to FIG. 1 we see a front view of a person wearing the head covering 100 of the present invention. The covering 2 is made of an inner and outer layer of plastic film forming an air trapping insulating means. The plastic is flexible and collapsible so that it can be folded flat when in a storage position. Similar material can be found as an insulating material in the construction industry. The tab 4 is adjustable to account for varying head sizes 8. Velcro™, neck and loop fastener 6 keeps tab 4 closed and the entire head covering assembly 100 fitting snuggly on the users head, FIG. 2 shows a perspective view of the cross brace 50 of the present invention which is inserted into the inside of head covering 2. The brace 50 is made of rigid material such as injection molded polyethelene plastic. The main spine 10 terminates at each end in a ninety degree bend tab 60, 62 having a horizontally disposed retaining post 12, 14. Spine 10 also contains a plurality of retaining arms 20, 22 that can removably retain warming packs 16, 18. Warming packs 16, 18 are known and available from Heatmax Corporation of Dalton, Ga. They are traditionally used as hand warmers for people who are in cold environments such as when skiing and the like. The compound in each pack is comprised of a mixture of iron powder, water, salt, activated charcoal and vermiculite. This combination creates a heat reaction that rises to approximately one hundred and twenty six degrees and lasts for three hours or more. The heat reaction takes place when air strikes the pack 16,18 after the user has removed the warming pack 16,18 from its air tight plastic wrapping. Cross brace assembly 50 is inserted into the insulated head covering 2 as shown in FIG. 3. The posts 12, 14 of cross brace 50 penetrate holes 11, 13 and thereby hold the cross brace 50 in position towards the upper inside top of the head covering 2. Heat waves 4 can then travel down to the users hair 46 and warm it, thereby helping the performance of an applied heat activated conditioning product such as Thermasilk heat activated conditioner manufactured by Helene Curtis of Chicago, Ill. FIG. 3 also shows a clear view of the double wall 40, 42 construction of head covering 2. The air 41 trapped within walls 40, 42 acts as an insulator thereby holding heat within the head covering 2.

In the above described and illustrated way, a person can use a heat activated hair conditioning product available in the marketplace and have the product work more effectively and easily because of the heat generating packs contained within the insulated head covering of the present invention. The user is free move about and to do other activities while the head covering of the present invention is doing its job. The head covering is reusable and the heat packs can be removed and replaced for multiple uses.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. Head Covering With Heat Generating Means comprising:

an insulated adjustable head covering;

a rigid cross brace attached to an upper inside of said head covering;

a plurality of heat generating packets removably attached to said cross brace;

said heat generating packets comprised of a combination of iron powder, water, salt, activated charcoal and vermiculite; and said heat generating packets packed in an air tight package which activate when removed from said air tight package.

2. Head Covering With Heat Generating Means as claimed in claim 1 wherein said heat generating packets produce heat of approximately 126 degrees F.

3. Head Covering With Heat Generating Means as claimed in claim 1 wherein said heat generating packets are removable and replaceable.

\* \* \* \* \*